US008246910B2

(12) United States Patent
Dhirani et al.

(10) Patent No.: US 8,246,910 B2
(45) Date of Patent: Aug. 21, 2012

(54) DIELECTRIC SENSING METHOD AND SYSTEM

(75) Inventors: Al-Amin Dhirani, Toronto (CA); Yoshinori Suganuma, Toronto (CA)

(73) Assignee: Universal Nanosensor Technologies Inc., Toronto, ON (CA)

( * ) Notice: Subject to any disclaimer, the term of this patent is extended or adjusted under 35 U.S.C. 154(b) by 639 days.

(21) Appl. No.: 12/225,154

(22) PCT Filed: Mar. 16, 2007

(86) PCT No.: PCT/CA2007/000429
§ 371 (c)(1),
(2), (4) Date: Jun. 18, 2009

(87) PCT Pub. No.: WO2007/104163
PCT Pub. Date: Sep. 20, 2007

(65) Prior Publication Data
US 2009/0273354 A1 Nov. 5, 2009

Related U.S. Application Data

(60) Provisional application No. 60/782,542, filed on Mar. 16, 2006.

(51) Int. Cl.
*G01N 27/00* (2006.01)
(52) U.S. Cl. ...... 422/82.01; 422/68.1; 422/50; 436/518; 436/524; 436/527; 436/807; 436/809; 435/7.1; 435/283.1; 435/287.1; 435/287.2
(58) Field of Classification Search ............ 422/50, 422/68.1, 82.01; 435/7.1, 283.1, 287.1, 287.2; 436/518, 524, 527, 807, 809
See application file for complete search history.

(56) References Cited

U.S. PATENT DOCUMENTS 4,216,451 A * 8/1980 Nishimura et al. ............. 334/15
(Continued)

FOREIGN PATENT DOCUMENTS

CA 1180759 1/1985
(Continued)

OTHER PUBLICATIONS

Haderka, "Permittivity and Conductivity Detectors for Liquid Chromatography", Journal of Chromatography, Apr. 24, 1974, vol. 91, pp. 167-179.

(Continued)

*Primary Examiner* — Melanie J Yu
(74) *Attorney, Agent, or Firm* — Lynn C. Schumacher; Hill & Schumacher

(57) ABSTRACT

Sensing device and method for detecting presence and concentration of generic target analytes of interest. The device and method are based on detecting changes in effective dielectric induced by the target analytes of interest. Applications of the invention include, but are not restricted to, detecting and characterizing the presence of chemical and/or biological target analytes of interest as well as detecting and characterizing target analytes of interest from a separation apparatus. In one embodiment of the invention, the device comprises at least two electrodes in a rigid architecture such as a solid surface, where the electrodes have sizes and inter-electrode spacings that are on the order of sizes of target analytes of interest to improve sensitivity of the device. Changes in effective dielectric and, therefore, capacitance induced by a presence of the target analytes of interest are measured electronically. The changes are used to detect the presence of the target analytes of interest and to characterize their presence.

34 Claims, 4 Drawing Sheets

U.S. PATENT DOCUMENTS

| | | | |
|---|---|---|---|
| 4,728,882 | A | 3/1988 | Stanbro et al. |
| 5,008,627 | A | 4/1991 | Tsutsuta et al. |
| 5,045,798 | A | 9/1991 | Hendrick |
| 5,082,627 | A | 1/1992 | Stanbro |
| 5,234,566 | A * | 8/1993 | Osman et al. ............ 204/403.06 |
| 6,521,109 | B1 | 2/2003 | Bartic et al. |
| 6,548,311 | B1 | 4/2003 | Knoll |
| 6,630,359 | B1 * | 10/2003 | Caillat et al. ...................... 438/1 |
| 6,847,216 | B2 | 1/2005 | Marszalek |
| 2002/0070114 | A1 | 6/2002 | Miles |
| 2003/0141189 | A1 | 7/2003 | Lee et al. |
| 2005/0052646 | A1* | 3/2005 | Wohlstadter et al. ......... 356/311 |
| 2007/0209977 | A1 | 9/2007 | Wilf et al. |

FOREIGN PATENT DOCUMENTS

| | | |
|---|---|---|
| CA | 2267281 | 4/1998 |
| CA | 2215164 | 11/2002 |
| CA | 2554997 | 8/2005 |
| EP | 1376111 | 1/2004 |
| JP | 08313577 | 11/1996 |
| WO | 88/09499 | 12/1988 |
| WO | 9928737 | 6/1999 |

OTHER PUBLICATIONS

Crabtree et al., "Shah Convolution Fourier Transform Detection", Anal. Chem. 1999, 71-2130-2138.

McReynolds et al., "Comparison of Hadamard Transform and Signal-Averaged Detection for Microchannel Electrophoresis", Anal. Chem. 2004, 76, 3214-3221.

McReynolds et al., "Shah and Sine Convolution Fourier Transform Detection for Microchannel Electrophoresis with a Charge Coupled Device", Anal. Chem. 2002, 74, 5063-5070.

Kwok et al., "Characterisation of Shah Convolution Fourier Transform Detection", Analyst, 2001, 126, 1640-1644.

Eijkel et al., "Wavelet Transform for Shah Convolution Velocity Measurements of Single Particles and Solutes in a Microfluidic Chip", Lab on a Chip, 2001, 1, 122-126.

Kaneta, T., "Hadamard Transform CE", Anal. Chem. Oct. 2001, 8 pages.

Kwok et al., "Shah Convolution Differentiation Fourier Transform for Rear Analysis in Microchip Capillary Electrophoresis", J. Chromatography A, 924, 2001, 177-186.

Nadherna et al., "Properties of the Contactless Impedance Detector with Insulated Wire Electrodes Placed Inside the Flowing Liquid Stream", Electroanalysis 19, 2007, No. 23, 2413-2418.

Tanyanyiwa et al., "High-Voltage Capacitively Coupled Contactless Conductivity Detection for Microchip Capillary Electrophoresis", Anal. Chem. 74, 2002, 6378-6382.

Wang et al., "Movable Contactless-Conductivity Detector for Microchip Capillary Electrophoresis", Anal. Chem. 2003, 75, 4475-4479.

Takeuchi et al., "Use of a Capacitance Measurement Device for Surrogate Noncontact Conductance Measurement", Talanta, 76, 2008, 617-620.

Kuban et al., "High-performance Liquid Chromatography with Contactless Conductivity Detection for the Determination of Peptides and Proteins Using a Monolithic Capillary Column", J. Chromatography A, 1176, 2007, 185-191.

Fu et al., "Fabrication and Testing of High-performance Detection Sensor for Capillary Electrophoresis Microchips", Biomed Microdevices, 2008, 10, 73-80.

Pumera, M., "Contactless Conductivity Detection for Microfluidics: Designs and Applications", Talanta, 74, 2007, 358-364.

Kuban et al., "A Review of the Recent Achievements in Capacitively Coupled Contactless Conductivity Detection", Analytica Chimica Acta, 607, 2008, 15-29.

Matysik, F., "Advances in Amperometric and Conductometric Detection in Capillary and Chip-based Electrophoresis", Microchim Acta, 2008, 160, 1-14.

Kuban et al, "Fundamental Aspects of Contactless Conductivity Detection for Capillary Electrophoresis. Part II: Signal-to-noise Ratio and Stray Capacitance", Electrophoresis, 2004, 25, 3398-3405.

Kuban et al, "Fundamental Aspects of Contactless Conductivity Detection for Capillary Electrophoresis. Part I: Frequency Behavior and Cell Geometry", Electrophoresis, 2004, 25, 3387-3397.

Karunanayake et al., "Capacitive Sensors for In-Vivo Measurements of the Dielectric Properties of Biological Materials", IEEE Trans. on Instrmentation and Measurement, 37, No. 1, Mar. 1988, 101-105.

Brust et al., "Self-Assembled Gold Nanoparticle Thin Films with Nonmetallic Optical and Electronic Properties", Langmuir, 1998, 14, 5425-5429.

Musick et al., "Electrochemical Properties of Colloidal Au-Based Surfaces: Multilayer Assemblies and Seeded Colloid Films", Langmuir 1999, 15, 844-850.

Musick et al., "Stepwise Construction of Conductive Au Colloid Multilayers from Solution", Chem. Mater., 1997, 9, 1499-1501.

Fishelson et al., "Studies on Charge Transport in Self-Assembled Gold-Dithiol Films: Conductivity, Photoconductivity, and Photoelectrochemical Measurements", Langmuir, 2001, 17, 403-412.

Tay et al., "Floating Resistivity Detector for Microchip Electrophoresis", Electrophoresis 2007, 28, 4620-4628.

Hu et al., "The Integration of Gold Nanoparticles with Semi-conductive Oligomer Layer for Development of Capacitive Immunosensor", Sensors and Actuators B, 106, 2005, 641-647.

Benningfield et al., "A Commercially Available Dielectric Constant Detector for Liquid Chromatography and Its Applications", J. Chromatographic Sc., vol. 19, Mar. 1981, 9pps.

"Construction of a Permittivity Detector for Liquid Chromatography", Methods of Analysis of Drugs of Abuse, Special Ed. May 1972, 2 pgs.

Haderka, S., "Role of the Mobile Phase Permittivity in the Use of the Capacitance Detectors in Liquid Chromatography", J. Chromatography, 52, 1970, 213-220.

Haderka, S., "Use of the Resonance Principle in the Permittivity Detectors for Liquid Chromatography", J. Chromatography, 54, 1971, 357-366.

Haderka, S., "The Prospects of Selective Detection by Capacitance Detectors in Liquid Chromatography", J. Chromatography, 57, 1971, 181-191.

Fuller et al., "On-line Process Liquid Exclusion Chromatography Applied to the Production of Styrene-Butadiene Copolymers", J. Chromatorgraphic Sc. 17, Dec. 1979, 661-665.

Stelzle et al., "Sensitive Detection of Protein Adsorption to Supported Lipid Bilayers by Frequency-Dependent Capacitance Measurements and Microelectrophoresis", Biochimica et Biophysica Acta, 981, 1989, 135-142.

Wohltjen, H., "Colloidal Metal-Insulator-Metal Ensemble Chemiresistor Sensor", Anal. Chem., 1998, 70, 2856-2859.

Joseph et al, "Self-Assembled Gold Nanoparticle/Alkanedithiol Films: Preparation, Electron Microscopy, XPS-Analysis, Charge Transport, and Vapor-Sensing Properties", J. Phys. Chem. B, 2003, 107, 7406-7413.

Joseph et al, "Chemiresistor Coatings From Pt- and Au-Nanoparticle/Nonanedithiol Films: Sensitivity to Gases and Solvent Vapors", Sensors and Actuators B, 98, 2004, 188-195.

Su et al., "Miniaturized Chemical Multiplexed Sensor Array", J. Am. Chem. Soc., 2003, 125, 9930-9931.

Leopold et al., "Growth, Conductivity, and Vapor Response Properties of Metal Ion-Carboxylate Linked Nanoparticle Films", Faraday Discuss., 2004, 125, 63-76.

Jospeph et al., "Gold-Nanoparticle/Organic Linker Films: Self-Assembly, Electronic and Structural Characterisation, Composition and Vapour Sensitivity", Faraday Discuss, 2004, 125, 77-97.

Patent Cooperation Treaty (PCT). International Search Report. PCT/CA2010/000310. Dated Jul. 19, 2010. Completed Jul. 6, 2010.

* cited by examiner

DIELECTRIC SENSING METHOD AND SYSTEM

CROSS REFERENCE TO RELATED U.S. APPLICATIONS

This patent application is a National Phase application claiming the benefit of PCT/CA2007/000429 filed on Mar. 16, 2007; which further and claims the priority benefit from, United States Provisional Patent Application Ser. No. 60/782, 542 filed on Mar. 16, 2006, in English, entitled DIELECTRIC SENSING METHOD AND SYSTEM, and which is incorporated herein by reference in its entirety.

FIELD OF THE INVENTION

The present invention relates to a method and device for detecting the presence of chemical and/or biological target analytes of interest using dielectric sensing.

BACKGROUND OF THE INVENTION

A huge amount of chemical substances are processed in many fields, including those related to chemicals, pharmaceuticals, biology and medicine. In such fields, there is frequently a requirement that a target analyte of interest has to be separated from a mixture. For example, in fields such as chemical and pharmaceutical industries, chemical analytes are synthesized, and chemical synthesis tends to generate reaction mixtures that contain target analytes of interest as well as other species such as (potentially multiple) by-products and unreacted reactants. As a further example, in biological, medical, food and other industries, mixtures that are readily obtained contain various target analytes of interest and other species.

Frequently, it is desired to detect and/or characterize (e.g. determine a concentration of) a target analyte of interest; e.g. detect and determine a concentration of bacteria in food, measure a concentration of glucose in blood, etc. Many other examples are readily apparent to those skilled in the art. It is quite common to detect and/or characterize target analytes of interest directly from mixtures. It is also quite common to subject mixtures to separation processes whereby target analytes of interest are obtained with increased purity to aid in their detection, characterization and further use.

Separation and/or detection methods include, but are not restricted to, thin film chromatography, flash column chromatography, high performance liquid chromatography (HPLC) and electrophoresis. Separation methods may be analytical in nature to characterize mixtures or preparatory in nature to generate separations in quantitative yields. To separate a target analyte of interest from a mixture, separation methods pass mixtures through various materials and exploit a fact that different species and target analytes of interest pass through the materials at different rates.

For example, in liquid chromatography, mixtures are passed through various packing materials in a column. Target analytes of interest and various other species travel through separatory materials at different rates, depending on various factors such as different interactions experienced by various species or target analytes of interest arising from a nature of solvents, chemical nature of packing materials, an existence and size of pores in the packing materials, etc. In a successful separation process, target analytes of interest and various other species in the mixtures exit the column at different times, and can thus be separated. If a target analyte of interest has a distinct visible colour, the time when the target analyte of interest exits a separation apparatus can be determined visually. If the target analyte of interest does not have a distinct visible colour, however, other physical properties of the target analyte of interest have to be measured to aid in its selection from other species in the mixture. Methods and devices that can yield quantitative measures for a degree of separation of target analytes of interest from other species are highly desirable.

Optical measurements are most frequently used for such purposes. For instance, surface plasmon resonance (SPR) is used to monitor binding of target analytes of interest to surfaces and thereby detect a presence of such target analytes. In chromatography and electrophoresis, optical spectroscopy using ultra-violet (UV) and/or visible light is frequently employed to obtain absorption spectra of target analytes of interest and other species and thereby monitor their separation. Depending on chemical natures and structures of target analytes of interest and other species, their absorption strength may be different. Apparatus for optical measurements can include UV lamps, lasers, lenses, detectors, and other optical elements and tend to be large and relatively expensive. Also, often target analytes of interest and other species do not have UV or visible absorption features that are suitable and optical methods cannot be utilized. Further, many biological target analytes of interest, for example proteins, are frequently obtained only in small quantities so that very high detection sensitivities and high-signal-to-noise ratio are required. To overcome these challenges, optical methods and devices rely on labels, for example, fluorescent labels. However, this requires modifying the target analyte of interest, which is usually undesirable, and requires significant labour, time and, as a result, expense. Optical devices and methods that rely on measurements of bulk index of refraction tend to be sensitive to temperature and pressure of solvents. For example, mechanical deformations induced by temperature and pressure changes result in changes in signal that compete with changes in signal induced by target analytes of interest. Also, when performing chromatography such as HPLC, for example, it is frequently desirable to use a gradient elution, that is, to use mixtures of solvents containing two or more components and to vary fractions of components present in the mixture systematically as the separation proceeds. Since the index of refraction of the solvent varies significantly as the fractions of components vary, it is difficult to detect small changes in index of refraction induced by small amounts of target analytes of interest. As a result, index of refraction measurements are not used with gradient elution.

A number of inventions are directed towards detecting a presence of target analytes of interest based on changes in electrical resistance (or equivalently resistivity, conductance or conductivity) of a circuit. U.S. Pat. No. 6,824,974 B2 teaches detection of a target analyte of interest using a biomolecule that spans a gap between two electrodes. Binding of a target analyte of interest changes conductivity between the two electrodes.

U.S. Pat. No. 6,458,327 B1 teaches an electronic device, especially a chemical sensor, comprising a nanoparticle structure configured such that a current path is defined through said nanoparticle structure and analyte molecules change the conductivity of the structure.

U.S. Pat. No. 5,194,133 discloses a sensor device for the analysis of a sample fluid comprising an elongated channel, a material in the channel causing separation of a sample fluid, enzymes, and pairs of sensing electrodes along the walls of the channel. Enzymes in the channel react with enzyme substrates in the sample fluid, changing conductivity of the sample fluid and thereby signalling a presence of the enzyme substrates.

U.S. Pat. No. 4,920,047 describes a method and apparatus for determining the presence of, the concentration of, or the absence of, immunologically active substances in liquid media by measuring any change of electrical impedance of an electrode. The electrode is provided with immunologically active substances, such as antigens or antibodies, which in turn provide binding sites for complementary immunologically active substances, such as antibodies or antigens, respectively. If the electrode is exposed to complementary immunologically active substances, binding sites become unavailable; otherwise, the binding sites remain available. The electrode is subsequently exposed to an enzyme that is also capable of binding to the binding sites and capable of generating an insoluble reaction product. The insoluble reaction product can deposit and adhere to the electrode thereby changing its impedance and indirectly signalling the presence of, the concentration of, or the absence of, complementary immunologically active substances in liquid media, such as water or saline.

Resistance-based methods and devices are limited by a competition between influences of target analytes of interest vs. those of media such as water, and the like which are conducting. As a result, sensitivity can be limited in devices and methods that require operation in such media and that attempt to detect target analytes of interest directly. To overcome such difficulties, devices and methods may employ amplification of sensitivity (e.g. through use of enzymes to generate significant product to signal detection) or removal of devices from such media; however, these approaches require additional steps and, therefore, resources such as time, expense, etc. Also, in chromatography applications such as HPLC, it is frequently desired to detect target analytes of interest that are non-conducting and that are dissolved in non-conducting media.

A number of inventions, therefore, have also been directed towards detecting a presence of target analytes of interest based on changes in electrical capacitance, C. Such inventions utilize a principle that capacitance is proportional to the dielectric constant of a medium in a region sensed by electric fields of the capacitor. If the region contains a mixture of two media, A and B, with respective dielectric constants $\in_A$ and $\in_B$, then the capacitance is proportional to an effective dielectric constant, $\in$, which is a function of $\in_A$, $\in_B$ and volume fractions of A and B. For a large parallel plate capacitor, approximately $C=\in A/d$, where A is area and d is separation of the parallel plates. The example of a parallel plate capacitor is used for illustrative purposes only and is not intended to limit the scope of this invention. The above formula for capacitance for a parallel plate capacitor assumes that the electric field is localized in the volume A·d between the parallel plates. In practise, for finite size plates, there is a fringe electric field that extends beyond edges of the parallel plates to length scales that are on the order of d; nevertheless, C is still proportional to $\in$. The impedance, $Z_C$, of a capacitor at a frequency, $\omega$, is $Z_C=(j\omega C)^{-1}$. When the capacitor is driven by a time dependent voltage, V, the voltage generates a time dependent electric field which senses $\in$ in a region. Depending on $\in$ sensed by the electric field, the electric field induces a polarization in the region, which in turn induces a time dependent charge on the capacitor. The resulting capacitative current, I, is $I=V/Z_C=j\omega CV$. To facilitate measurement, the capacitative current is typically amplified, by an amount $R_G$, generating a measured voltage, $V_G=j\omega R_G CV$. For a parallel plate capacitor, $V_G=j\omega R_G \in AV/d$; thus, the measured voltage across the capacitor is proportional to $\in$.

Accordingly, in capacitance-based methods and devices, a change in E generates a change in $V_G$. Such a change in $\in$ occurs, for example, when a target analyte of interest with a first dielectric constant enters the region sensed by the electric field and displaces media in the region with a second effective dielectric constant of a different value. If the target analyte of interest has a small dielectric constant and the media includes solvents such as water, saline, electrolytes, and the like, which have large effective dielectric constants by virtue of their non-insulating nature, large changes in $\in$ can be realized. If a target analyte of interest is located in the region sensed by the electric field, and an object (for example a conducting bead) with a large effective dielectric constant is attached to the target analyte of interest, thereby displacing media with smaller effective dielectric constant, again large changes in $\in$ can be generated. Such large changes in $\in$ have been exploited in a number of devices and methods designed to detect target analytes of interest.

U.S. Pat. No. 6,764,583 B2 teaches impedance measurements between electrodes in an electric field to detect the presence of pathogens trapped in the electric field. The pathogens change the impedance between electrodes by changing the dielectric material between the electrodes. Subsequently in U.S. Pat. No. 6,846,639 B2, Miles et al. teach using beads coated with antibodies to aid in the detection of pathogens. The beads stick to pathogens trapped in the electric field, producing an additional change in the impedance.

United States Patent Publication No. 2005/0227373 A1 discloses a method and device for high sensitivity detection of the presence of DNA and other probes. A presence of a target sample on a substrate is capacitatively detected by binding the target sample to selective binding sites on the substrate, the target sample being directly or indirectly labelled with conducting labels, and capacitatively detecting the presence of the conductive labels.

United States Patent Publication No. 2002/0192653 A1 is directed towards impedance-based chemical and biological imaging sensor apparatus and methods. The imaging sensor consists of a two-dimensional array of impedance electrode elements separated from chemical or biological samples contained in fluids by a fluid-impervious layer. Changes in capacitance due to impedance changes at an outer surface of the fluid-impervious layer are detected during interrogation of electrode elements. The imaging chip does not respond to dry pollen, but if the particles are suspended in dilute phosphate buffer and a trace surfactant, the particles can be imaged in contrast.

U.S. Pat. No. 5,846,708 teaches a method and apparatus for identifying molecular structures within a sample substrate using a monolithic array of test sites. In an electrical embodiment of the invention, a substance having a molecular structure is applied to the test sites, each test site having a probe capable of binding (hybridizing) with a known molecular structure. Hybridized molecules can be detected, in accordance with one embodiment of the invention, by sensing the change in the dissipation of a capacitor formed at the test site. At the resonance frequency of a DNA molecule in aqueous solution, the imaginary part of $\in$ can be approximately 10 to 100 times larger than its value for an aqueous solution without the DNA. The patent teaches that an LCR meter may be used to measure the resistance.

U.S. Pat. No. 5,187,096 discloses an apparatus and method for monitoring cell-substrate impedance using an array of electrode pairs. Each electrode pair includes a large counter electrode and a small active electrode. An AC current is applied between electrodes of each pair, while the voltage is monitored using a phase sensitive detector. Cells are cultured on the small electrodes. As the cells attach and flatten out on the electrode surface, they cause large changes in electrical impedance of the system.

United States Patent Publication No. 2006/0216203 is directed to a multi-well sample module having integrated impedance measuring electrodes which allow for the generation of an electric field within each well and the measuring of a change in impedance of each of the wells contents. The electric field generated by the electrodes extend from the electrodes roughly to the gap between the electrodes. Cells experience this electric field. Measurement of the total current allows calculation of the cell impedance from the impedance measurement. The impedance measurement is performed by measuring the current resulting from an applied alternating voltage. Both the magnitude and phase are part of the impedance.

U.S. Pat. No. 4,822,566 discloses an apparatus for detecting the presence and/or measuring the concentration of an analyte in a fluid medium. The apparatus relies on biospecific binding between a biochemical binding system and the analyte to change the dielectric properties of a capacitative affinity sensor. The biological affinity sensor is optimized by: (1) adjusting the thickness and dielectric properties of a passivation layer to generally match the impedance of the biological binding system; and (2) minimizing the double layer capacitance (of the non-insulating fluid system) in order to maximize capacitance changes associated with the biological binding system.

It is desirable to have a general method and device that are label-free and capable of measuring even small changes in effective dielectric constant. As an example, in chromatographic separations, target analytes of interest may be insulating and dissolved in solvents such as alkanes or benzene, which are also insulating. In such cases, differences between effective dielectric constants of solvents and of mixtures of solvents and target analytes of interest are small. To generate sufficiently large changes in measured voltages even for such applications, using a parallel plate capacitor geometry as an example, it is desirable to chose advantageously $R_G$, $\omega$, A, d, and V. Increasing V and $R_G$ results in larger changes in measured voltages. Increasing $\omega$ also results in larger changes in measured voltage. Measurement of voltages at various $\omega$ and regression analysis of such measurements results in increased accuracy in determination of changes in $\in$. A and d (and in general for non-parallel plate capacitors, the volume sensed by the electric field) can be engineered to optimize changes in measured voltages. If the volume sensed by the electric fields is too small, then only a small portion of space occupied by target analytes of interest will be sensed, which is undesirable. If the volume is too large, then the change in $\in$ induced by the target analytes of interest will be small, which, too, is undesirable. An intermediate choice is preferred. In one optical embodiment of the present invention, near field optics principles can be used to confine electric fields to much smaller volumes than in far field optics. By engineering sizes, shapes, spacings, orientation, etc of electrodes it is possible to engineer electric fields in electronics. Therefore, it will be apparent to those skilled in the arts that optimization of the electric fields for a given target analyte of interest is possible and desirable to detect changes in $\in$, not just in electronics but in electromagnetics generally.

In order to increase changes in $V_G$ induced by changes in $\in$, in turn induced by a target analyte of interest, it is desirable to maximize the fraction of volume occupied by the target analyte of interest in the region sensed by the electric field. This can be accomplished by engineering electric fields as disclosed above and further by incorporating into the region sensed by the electric field, atomic species, functional groups, molecules, and more generally chemical and/or biological discrimination elements that interact with target analytes of interest. For example, if the region sensed by the electric field is at or near a surface and the target analyte of interest is a strand of DNA, then functionalizing the surface with a complementary strand of DNA can generate higher concentrations of the strand of DNA near the surface than in solution. Many interactions can be exploited in such a fashion to increase concentrations of target analytes of interest and will be apparent to those skilled in the arts. The interactions include electromagnetic and/or quantum interactions such as those that give rise to antigen-antibody paring, DNA hybridization, and interactions between other biological species, various chemical phenomena such as bonding, solubility, and the like. Such interactions generate various degrees of chemical and/or biological discrimination and will be apparent to those skilled in the arts. Such increases of concentrations have an advantageous feature of overcoming a problem that arises generally for devices and methods that rely on measurements of bulk properties such as conductivity and bulk dielectric constant. As solvent composition changes during gradient elution, there arises a large change in bulk properties, making detection of small changes generated by target analytes of interest difficult. Increasing the volume fraction of target analytes of interest in the region sensed by the electric field has advantageous effects of reducing the volume fraction of the solvents and mitigating the detrimental influence of changing solvent composition.

If media in which target analytes of interest are dissolved are non insulating, the media will have finite conductance and therefore resistance. Hence they generate dissipation in the capacitance, a real component in the measured voltage, a complex component in $\in$ and a complex component in the measured voltage that involves both resistance and capacitance. As resistance decreases, current increases, leading to saturation of electronics especially if $R_G$ is increased to detect small changes in $\in$. Determination of capacitative impedance, and therefore, small changes in $\in$ become difficult. To address this problem, it is desirable to develop methods and devices employing an insulating region that impedes external current flow so as to permit detection of even small changes in $\in$.

A simple-to-use, inexpensive, label-free, portable, quantitative, robust, sensitive, structurally and chemically stable and generally applicable invention for detecting, distinguishing, and characterizing target analytes of interest and other species is, therefore, highly desirable. In particular, it would be highly desirable to have an invention that is based on a property universally possessed by all target analytes of interest (for example, $\in$) and that is insensitive to changes other than those induced by target analytes of interest. Such an invention would have many other applications, besides monitoring separation of mixtures. These applications include, but are not restricted to, monitoring interactions between surfaces functionalized with chemical and/or biological discrimination elements (such as unfunctionalized molecules, mono-functionalized molecules, bi-functionalized molecules, poly-functionalized molecules, oligomers, polymers, catalysts, cells, bacteria, viruses, enzymes, proteins, heptans, saccharides, lipids, glycogens, enzyme inhibitors, enzyme substrates, neurotransmitters, hormones, antigens, antibodies, DNA, and/or RNA), and pharmaceutical, biological and/or medically related compounds (such as drugs, DNA, RNA, proteins, antigens, antibodies, heptans, saccharides, lipids, glycogens, enzyme inhibitors, enzyme substrates, neurotransmitters, hormones, viruses, bacteria, cells, etc.) The invention can also be used for quality control tests in which results obtained using a control system are compared with those obtained using a test system. Such tests would be useful to monitor whether a chemical has become contaminated for instance. The invention can further be used in tests for monitoring water. Other uses for such an invention will be apparent to those skilled in the arts.

SUMMARY OF THE INVENTION

It is a primary object of the present invention to provide a dielectric sensing device and method. In one embodiment of the invention, the device includes at least two electrodes integrated on a monolithic architecture to ensure rigidity and mechanical stability. A time-dependent voltage is applied to at least one of the electrodes and a current induced by the time-dependent voltage is measured. The current may be amplified by electronic circuits and its magnitude and phase relative to those of the voltage can be measured. Such measurements provide information about the capacitance of the electrodes. The electrodes are fabricated such that their sizes and/or separations are, for example, similar to size scales of target analytes of interest so as to improve signal-to-noise ratio in capacitance measurements. For example, electrodes with sizes and/or separations that are on a nanometer scale may be used when detecting target analytes of interest that are nanometers in size. If nanometer-sized target analytes of interest form larger structures such as multilayers or other aggregates, then electrodes with sizes and/or separations that are correspondingly larger in size are preferred. When a target analyte of interest approaches said electrodes, capacitance measured at the electrodes may change due to a change in effective dielectric constant sensed by the electrodes. To facilitate sufficient amplification of capacitative current and, therefore, to facilitate detection of small changes in effective dielectric constant, it is advantageous to increase the resistive component of conductance. Accordingly, the invention advantageously employs a sufficiently insulating region that impedes external current flow to and/or from said electrodes.

Chemical and/or biological discrimination elements can be employed to improve detection of target analytes of interest. When a target analyte of interest approaches said electrodes and interacts with the chemical and/or biological discrimination elements for a period of time, a change in effective dielectric constant sensed by the electrodes occurs. Qualities of the change, such as its magnitude, duration, robustness, specificity, selectivity, sensitivity, etc., can be enhanced through interactions between the chemical and/or biological discrimination element and target analytes of interest. As examples, interactions between nonpolar target analytes of interest are favoured when nonpolar chemical and/or biological discrimination elements are used; interactions between polar target analytes of interest are favoured when polar chemical and/or biological discrimination elements are used; interactions between antigen target analytes of interest are favoured when conjugate antibody chemical and/or biological discrimination elements are used; etc.

The chemical and/or biological discrimination element may be, for example, bound to the rigid architecture between electrodes, to one electrode or to a plurality of electrodes. Furthermore, in this embodiment of the invention, use of electronic circuit methods for capacitance measurements affords several advantageous features, including miniaturization, integration, portability, high signal-to-noise ratio, high sensitivity, ease of availability of components, an existence of a wide selection of components, modularity and low fabrication cost.

In one aspect of the present invention there is provided a sensing device for sensing a target analyte of interest, comprising,
sensing device for sensing a target analyte of interest, comprising,
a) a means for applying a time-dependent electric field in a region about a first element from which said electric field emanates to sense an effective dielectric constant; and
b) a detection means for detecting a change in a temporal response caused by a change in said effective dielectric constant induced by said target analyte of interest in said region, wherein said region;
i) is held fixed by means of a rigid architecture; and
ii) has a size that is sufficiently large to sense a substantial portion of the target analyte of interest and sufficiently small so as to generate usable sensitivity and signal-to-noise ratio; and
c) a sufficiently insulating region that impedes external current to and/or from said first element so as to permit detection of said change in said temporal response.

The device may include at least one chemical and/or biological discrimination element.

The device may also accommodate a material through which the target analyte of interest and other species travel at different rates.

In another aspect of the present invention there is provided a method for
sensing a target analyte of interest, comprising the steps of;
applying a time-dependent electric field in a region about a first element from which said electric field emanates to sense an effective dielectric constant; and
detecting a change in a temporal response caused by a change in said effective dielectric constant induced by said target analyte of interest in said region and
determining a presence or absence of said target analyte of interest based on said change in said effective dielectric constant, wherein said region is
held fixed by means of a rigid architecture;
has a size that is sufficiently large to sense a substantial portion of the target analyte of interest and sufficiently small so as to generate usable sensitivity and signal-to-noise ratio; and
comprises a sufficiently insulating region that impedes external current flow to and/or from said first element.

The method may include using at least one chemical and/or biological discrimination element located in said region located about the first element.

The method may include using a material through which a target analyte of interest and other species travel at different rates.

The present invention also provides a separation apparatus, comprising;
a material through which a target analyte of interest and other species travel at different rates;
a sensing system for sensing the target analyte of interest comprising a sensing device, a time-dependent electric field sensing an effective dielectric in a region, a first element from which said electric field emanates into said region to sense said effective dielectric, a means for detecting a change in a temporal response of said sensing device caused by a change in said effective dielectric induced by said target analyte of interest, wherein said region
is held fixed by means of a rigid architecture;

has a size that is sufficiently large to sense a substantial portion of the target analyte of interest and sufficiently small so as to generate usable sensitivity and signal-to-noise ratio; and comprises a sufficiently insulating region that impedes external current flow to and/or from said first element.

The separation apparatus may include at least one chemical and/or biological discrimination element located in said region about the first element.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Generally speaking, the systems described herein are directed to sensing devices and methods that can be used for detecting various kinds of target analytes of interest. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to sensing devices and methods.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region.

The present invention has a number of uses. The following are presented just by way of example and are not to be construed as limiting or defining the invention.

Figure 1:
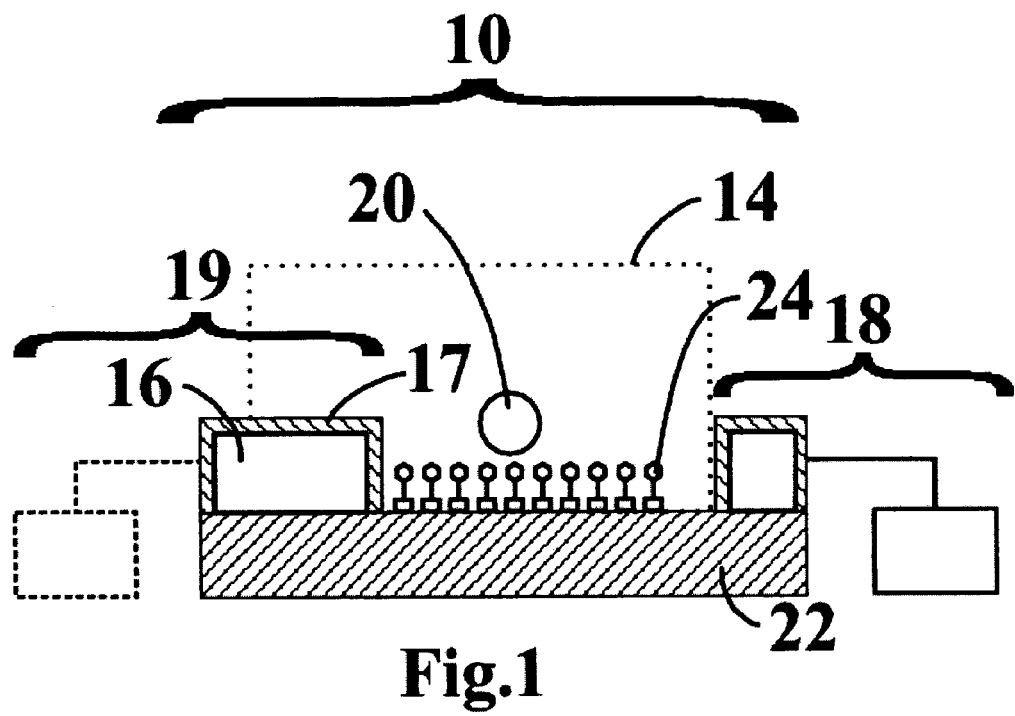
FIG. 1 shows an embodiment of a dielectric sensing device produced in accordance with the present invention for detecting target analytes of interest using changes in dielectric behaviour of the sensing device when the target analytes of interest are present.

This invention pertains to a novel sensing device and method that can be used for detecting various kinds of target analytes of interest. Referring to FIG. 1, a capacitive sensing device constructed in accordance with the present invention is shown generally at 10. The sensing device 10 comprises a number of features: a time-dependent electric field sensing a dielectric in a region 14, a first element 16 from which the electric field emanates to sense the dielectric, a detection means 18 for detecting a change in a temporal response of the sensing device 10 caused by a change in the dielectric region 14 in turn induced by the target analyte 20 of interest, wherein the dielectric region 14 is held fixed by means of a rigid architecture 22, has a size that is sufficiently large to sense a substantial portion of the target analyte 20 of interest and sufficiently small so as to generate usable sensitivity and signal-to-noise ratio, and comprises at least one chemical and/or biological discrimination element 24 to improve selectivity, sensitivity and specificity in detecting target analytes of interest. The time-dependent electric field may be an oscillating electric field. The chemical and/or biological discrimination element 24 may comprise at least one of unfunctionalized molecules, mono-functionalized molecules, bi-functionalized molecules, poly-functionalized molecules, oligomers, polymers, catalysts, cells, bacteria, viruses, enzymes, proteins, heptans, saccharides, lipids, glycogens, enzyme inhibitors, enzyme substrates, neurotransmitters, hormones, antigens, antibodies, DNA, and/or RNA.

The detection means 18, rather than being distinct from the first element 16, may be an integrated detection means 19 at least partially integrated with the first element 16 or may be an integrated detection means at least partially integrated with the rigid architecture 22. A sufficiently insulating region 17 impedes external current to and/or from said first element 16 so as to permit detection of said change in a temporal response.

Figure 2:
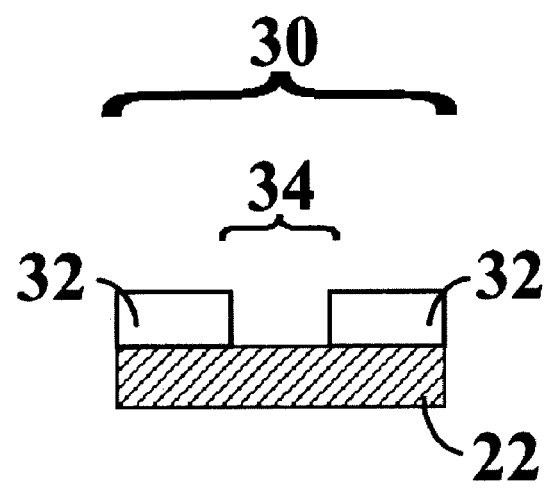
FIG. 2 shows another embodiment of a dielectric sensing device.

In one embodiment of the invention shown generally at 30 in FIG. 2, the sensing device comprises two or more electrodes 32, the relative positions of the electrodes being fixed with respect to one another by virtue of a rigid architecture 22. For example, in a parallel plate capacitor model, the electrodes possess a mutual capacitance, C, approximately given by $C = \in A/d$, where $\in$ is a dielectric constant, A is the cross-sectional area of the electrodes, and d is inter-electrode separation. In general, the electrodes possess a mutual capacitance that is proportional to an effective dielectric constant times geometric factors. When a time-dependent voltage is applied to the electrodes 32, a time-dependent electric field is generated. The electric field is concentrated in a region 34 between the electrodes, but possesses significant magnitude also beyond edges of the electrodes 32. In a parallel plate capacitor model, for example, the electric field extends beyond edges of the electrodes on a length scale that is on an order of a few multiples of d. A substantial benefit of fixing the relative positions of the electrodes 32 by virtue of a rigid architecture 22 is that undesirable noise arising from changes in capacitance due to changing geometrical factors are thereby substantially reduced. Signals in changes in capacitance arising from changes in dielectrics sensed by the electric fields are then more easily detected.

Electrodes 32 may be directly soldered to the architecture 22. In one embodiment of the invention, a glass slide is used as the architecture 22, and the electrodes 32 comprise indium, as indium strongly adheres to the glass slide, melts at relatively low temperature, and, thus, is easily soldered.

In another embodiment, the architecture 22 is placed in a vacuum chamber, and the electrodes 32 are deposited onto the architecture 22 via thermal evaporation or chemical vapour deposition through shadow masks, which determine boundaries of the electrodes 32. Through a use of masks, lithography and related patterning methods well known to those skilled in the arts, electrode sizes and inter-electrode spacings can be selected to range from millimetres down to submicron length scales.

By depositing very thin films, it is possible to form granular films on the architecture 22. Such granular films can be construed as comprising a plurality of electrodes forming a network of electrodes. In this manner it is possible to fashion electrodes with sizes and inter-electrode spacings that can approach fractions of a nanometer in size. Materials from which electrodes can be formed include, but are not restricted to, various semiconductors and metals, such as gold, aluminium, and silver. If necessary, adhesive layers for the electrodes may be deposited between the electrodes 32 on the rigid architecture 22. Chromium or silanes, for example, may be used for the adhesive layers.

In one embodiment, the electrodes 32 may be sufficiently insulated by a region 17 (FIG. 1) by incorporating in the region 17 materials such as organic compounds (e.g. self-assembled monolayers, polymers, and the like), and/or inorganic compounds (e.g. such as natural oxides of the electrodes, silicon nitride, silicon oxide, and the like).

Figure 3:
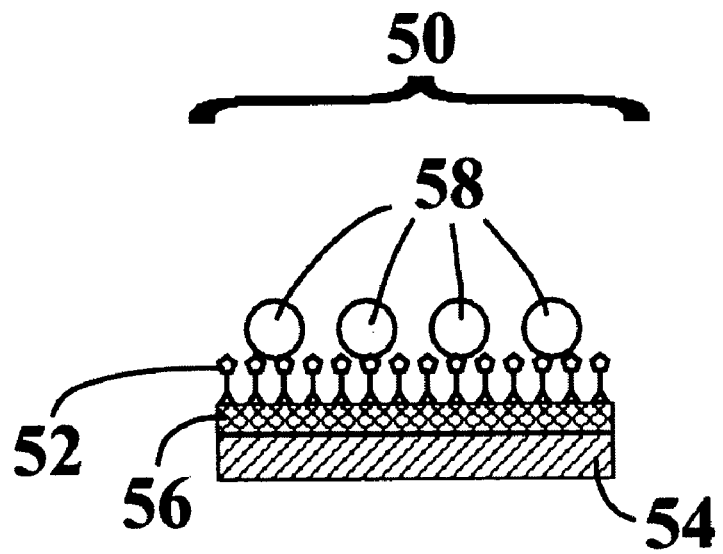
FIG. 3 shows another embodiment of a dielectric sensing device.

In yet another embodiment of the invention shown generally at 50 in FIG. 3, bifunctional molecules may be used to self-assemble the electrodes. Bi-functional molecules 52, for example, amino-silanes and mercapto-silanes, may be self-assembled onto a rigid architecture 54 with an oxide 56, such as silicon oxide or aluminium oxide. Self-assembly is driven by interactions between a first functionality, such as silane, and oxides. A second functionality, for example, amino- or thiol-groups, may be used to attach structures such as metallic nanoparticles 58, where the metallic nanoparticles may be considered as forming a self-assembled network of electrodes.

Figure 4:
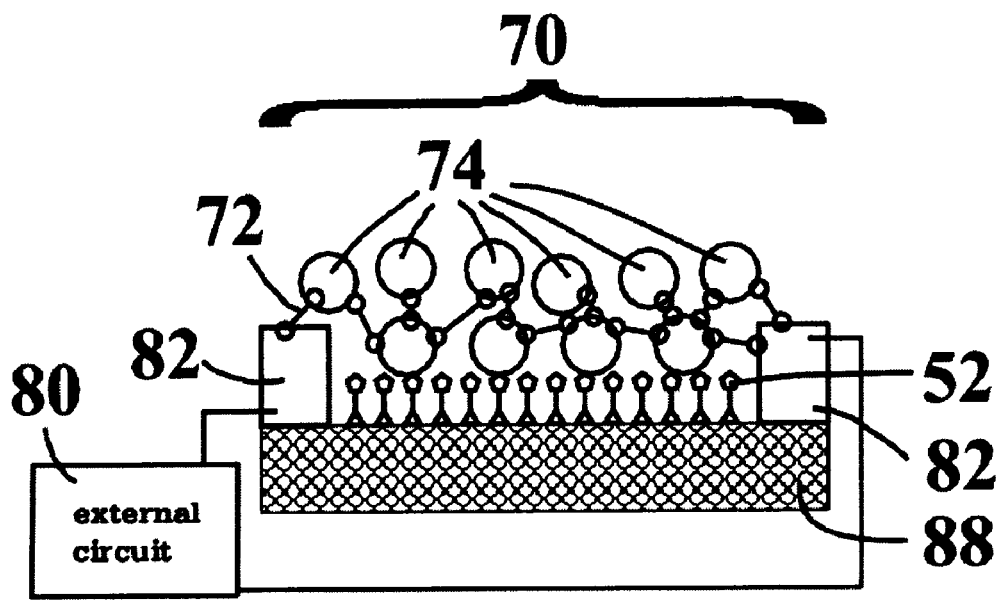
FIG. 4 shows another embodiment of a dielectric sensing device.

In a further embodiment shown generally at 70 in FIG. 4, the device 70 includes self-assembled network of nanoparticles, self-assembled onto a rigid architecture 88 with the aid of bifunctional molecules 52. The self-assembled network of nanoparticles is extended through repeated use of self-assembly using, alternately, bi-functional molecules 72, such as diamines and dithiols, for example, and nanoparticle structures, such as metallic nanoparticles 74, for example. The bifunctional molecules 72 are preferentially chosen to be sufficiently insulating so as to enable detection of changes in dielectric induced by target analytes of interest. Thus, in an embodiment the rigid architecture comprises nanoparticles connected by bi-functional molecular linkers that are sufficiently insulating so as to impede external current to and/or from the first element and so as to permit detection of said change in said temporal response.

For convenient attachment of electrodes to a detection means such as an external circuit 80, the electrodes may be electrically connected to conducting pads 82 formed by methods such as evaporation, soldering, chemical vapour deposition, and the like.

A voltage applied to the electrodes induces electric fields in regions between, and in a neighbourhood of, the electrodes. A presence of target analytes of interest in these regions will perturb the electric fields via the dielectric constant of the target analytes of interest, provided it modifies the effective dielectric constant sensed by the fields. Since capacitance, in general, is proportional to an effective dielectric constant, the presence of the target analytes of interest can be sensed by monitoring the capacitance of the electrodes. The capacitance can also be modified by changing inter-electrode separation.

As mentioned before, an advantageous feature of the present invention is that the region sensed by the time-dependent electric fields is held fixed by means of a rigid architecture 88. In one embodiment of the invention, the electrodes' positions are fixed with respect to each other via a rigid architecture 88 and thereby such undesirable changes in capacitance due to changing geometrical factors are eliminated.

Figure 5:
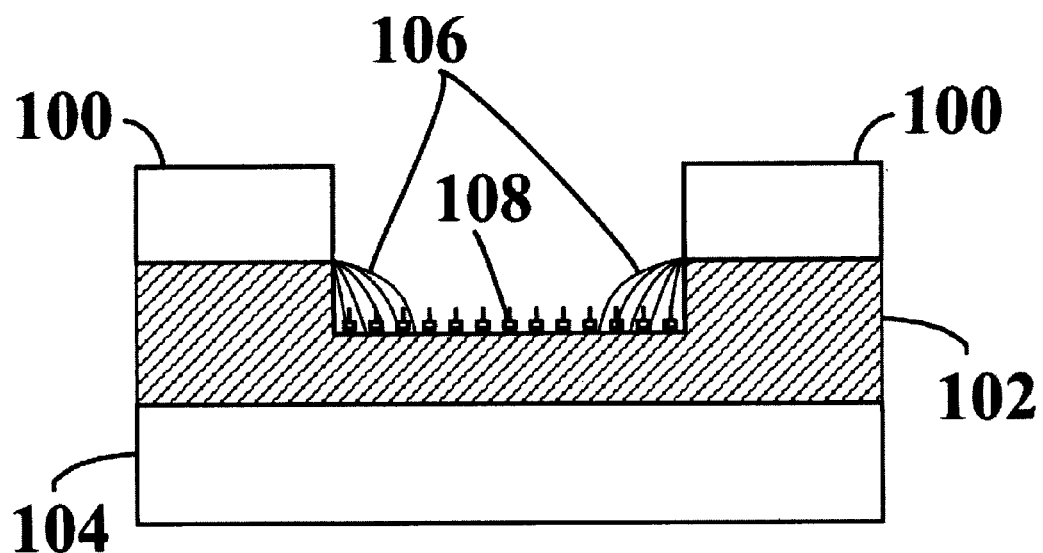
FIG. 5 shows another embodiment of a dielectric sensing device.

In another embodiment of the invention shown in FIG. 5, the sensing device comprises at least one electrode 100 on a rigid architecture, wherein the rigid architecture comprises a semiconducting layer 104 and a sufficiently insulating region 102 that sufficiently impedes external current to and/or from said electrode 100. The insulating region 102, which may comprise inorganic and/or organic materials such as silicon oxides, silicon nitrides, self-assembled films, and the like, may be grown or deposited on a semiconducting layer 104.

The electrode 100 is preferably fabricated so as to minimize its foot print over the insulating region 102, which foot print provides a measure of electric fields that are not available for sensing target analytes of interest. The electrode 100 is simultaneously also preferably fabricated so as to generate significant electric field in a region 106 about the electrode, which electric field is available and suitable to sense an effective dielectric constant and/or changes in effective dielectric constant related to target analytes of interest. For example, edges of the electrode 100 may be fabricated such that they are suitably long by fabricating correspondingly long electrodes using slits, masks, evaporation, lithography, and plating or other methods and apparatus well known to those skilled in the art.

Figure 6:
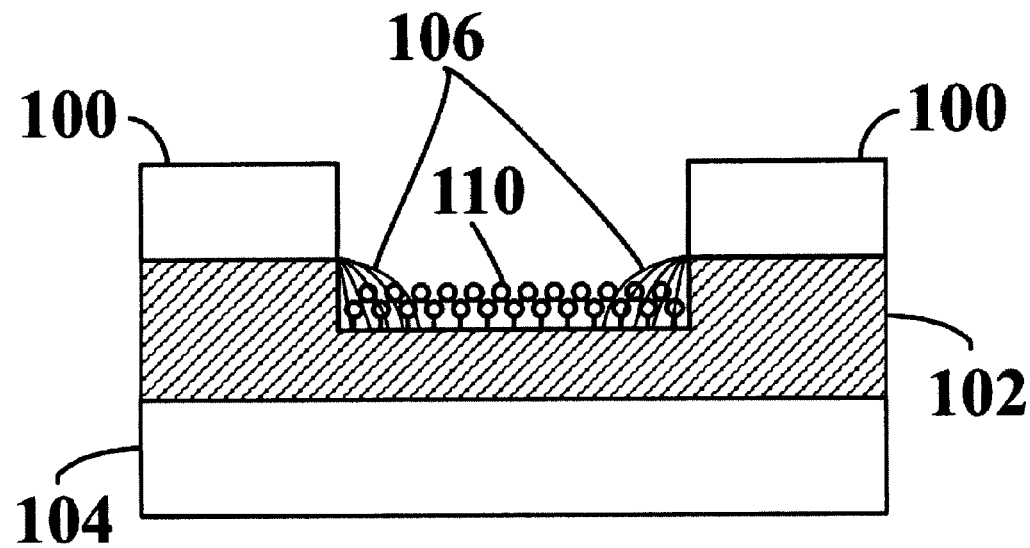
FIG. 6 shows another embodiment of a dielectric sensing device.

As shown in FIGS. 5 and 6, the insulating layer 102 may be formed with a surface profile to give wells with raised walls and the electrode formed on the sides of the raised walls.

Reducing the foot print has consequences of decreasing the relative contribution of electric fields that generate stray capacitances and simultaneously of increasing the relative contribution of electric fields which emanate to sense an effective dielectric constant in a region 106 about electrode 100 near the walls of the wells. Both consequences can increase the signal-to-noise background. The height of region 106 preferentially has a size that is sufficiently large to sense a substantial portion of the target analyte of interest and sufficiently small so as to generate usable sensitivity and signal-to-noise ratio. For example, if the chemical and/or biological discrimination element includes a hydrophobic moiety such as octadecylsilane, and the target analyte of interest is a hydrophobic molecule that can form multilayers of a few nanometers in thickness, the height of region 106 preferentially has a height that is sufficiently large to sense a substantial portion of the multilayer and sufficiently small so as to generate usable sensitivity and signal-to-noise ratio. This example is chosen from applications relating to high performance liquid chromatography (HPLC); however, many such examples from chemistry and/or biology will be apparent to those skilled in the art. In the embodiment shown in FIG. 5, when a time dependent voltage is applied between the electrode 100 and the semiconducting layer 104, electric fields emanate to sense an effective dielectric constant in a region 106 about electrode 100.

Target analytes of interest entering region 106 change the capacitance between electrode 100 and the semiconducting layer 104 by changing the effective dielectric constant of region 106. Such changes in capacitance can be detected by measuring the out-of-phase components of current response to the time-dependent voltage. Due to interaction between target analytes of interest and the chemical and/or biological discrimination elements 108, chemical and/or biological discrimination elements 108 in region 106 can increase the fractional volume of target analytes of interest in region 106 relative to that outside region 106, facilitating detection.

In a further embodiment of the invention shown in FIG. 6, a material 110 with a larger dielectric constant than that of insulating region 102 is attached to the surface of the sensor at least in region 106. Material 110 can serve as a convenient scaffolding for attaching chemical and/or biological discrimination elements and can serve to augment electric fields in region 106. Examples of material 110 include various self-assembled nanostructures (such as nanoparticles, for instance), molecules, as well as deposited organic and/or inorganic films.

Sensitivity of the sensing device in the present invention relies on a size of the region probed by the electric field. For example, regions probed by electric fields are determined by sizes of the electrodes and inter-electrode separation. Therefore, to accomplish efficient detection of target analytes of interest at sufficient sensitivity and signal-to-noise ratio, a size scale of the region should be sufficiently large to sense a substantial portion of the target analyte of interest and sufficiently small so as to generate usable sensitivity and signal-to-noise ratio.

A size scale of target analytes of interest may range from nanometer to sub-millimeter. Recent advances in chemical synthesis enable preparation of nanostructured materials such as metallic nanoparticles. In one embodiment of the present invention, the sensing device may comprise metallic nanoparticles which act as a plurality of nanoscale electrodes for detecting nanometer scale target analytes of interest. Since these nanostructured materials may be chemically self-assembled to produce the sensing device without resorting to expensive micro-lithographic techniques, rapid and inexpensive production is possible. In another embodiment of the present invention, regions sensed by electrodes can be tailored, through electrodes' sizes and inter-electrode separation using standard lithography methods well known to those skilled in the art.

In one embodiment, electrodes may be fashioned to probe a region that is sufficiently large to sense a substantial portion of an E coli bacterium (which is typically 5 micrometers in size) and sufficiently small so as to generate usable sensitivity and signal-to-noise ratio.

In still another embodiment of the present invention, the region is sufficiently large to sense a substantial portion of a bacterial virus or phage (which is typically 0.5 micrometer in size) and sufficiently small so as to generate usable sensitivity and signal-to-noise ratio. These embodiments are provided by way of example only, and do not define or limit the invention.

The present invention uses measurements that are sensitive to dielectrics to detect target analytes of interest. For example, in one embodiment of the invention, a time-dependent-voltage (for example, a sinusoidal voltage) may be applied to electrodes and a resulting current with a similar time-dependence may be measured using phase-lock detection. Since current is detected only at multiples of the same frequency at which the voltage is modulated, noise may be reduced significantly, and as a result, minute changes in capacitance may be detected. Capacitance is proportional to an effective dielectric constant which in turn is a function of dielectric constants of various substances in a capacitor. Therefore, changes in the effective dielectric constant induced by the presence of a target analyte of interest and sensed by electric fields of a capacitor give rise to change in capacitance. A change in capacitance in turn induces a change in phase between the modulated voltage and current and can be measured by the phase-lock detection method. The change in capacitance induced by change in concentration of target analytes of interest may be used for detecting the concentration of such target analytes.

Detection of target analytes of interest through changes in dielectric does not require passage of "external current". "External current" is taken to mean an irreversible electric current that does not store energy in a circuit. External current flows even in response to a time independent voltage, a ratio of applied time-independent voltage to magnitude of external current being the resistance. The dielectric sensing system, on the other hand, functions by polarization. For example, in one embodiment of the invention, upon application of a time-dependent voltage, capacitor electrodes become polarized due to electric fields between electrodes.

The invention includes a presence or use of a sufficiently insulating region that impedes external current to and/or from a region about an element from which an electric field emanates to sense an effective dielectric constant. The insulating region serves to increase signal-to-noise ratio when sensing dielectric constants. In one application of the invention, the dielectric sensor is exposed to a solution that contains target analytes of interest and ionic species. In general, upon exposure to a time-dependent electric field, the ionic species can migrate and often be oxidized or reduced, giving rise to significant in-phase response in the detection means. The significant in-phase response makes measurements of small out-of-phase response difficult. For example, it is frequently desirable to amplify significantly the small out-of-phase response; however, significant amplification leads to saturation due to the significant in-phase response. Therefore, the insulating region can facilitate improved sensitivity of the device to the effective dielectric constant and changes thereof.

In one embodiment of the invention, electrodes may comprise nanoparticles, which may be connected by bifunctional molecular linkers. Various choices of the molecular linker may be used: if shorter molecules are used, then external current may flow between nanoparticles by way of quantum tunneling and thermally assisted processes. Using sufficiently long, insulating molecules, external current can be substantially reduced. In both cases, polarization current may flow. Since capacitance measurements may use this polarization current, circuits do not have to be conductive; that is, linker molecules which are insulating and do not permit measurable external current flow can be still used in the present invention.

Chemical and/or biological discrimination elements 24 (see FIG. 1) may be exploited to improve selectivity, specificity and sensitivity in detecting target analytes of interest. The chemical and/or biological discrimination elements can be bound to the architecture, electrodes or both. An important requirement to enable sensing, however, is that the discrimination element's location must enable binding of the target analyte of interest in regions 14 or 106. The discrimination elements 24 include various chemical species with or without functional groups. For instance, a discrimination element with a polar functional group may aid in discriminating in favour of polar target analytes of interest and against non-polar species. The discrimination elements may include chemical species such as non-functionalized molecules, functionalized molecules, oligomers, and polymers as well as various biological assemblies, such as cells, bacteria, viruses and/or smaller biological components such as enzymes, proteins, antigens, antibodies, DNA, RNA, and the like. In one embodiment, the discrimination elements may be incorporated via self-assembly, whereby the discrimination element has a function group enabling attachment of the discrimination element to the sensing device and the discrimination element, not withstanding being attached to the sensing device, can interact with a target analyte of interest. Non-specific interactions with other species can be recognized by rinsing the sensing device.

The following example is provided for an illustrate purpose only and should not be considered to limit the claimed invention.

EXAMPLE

Figure 7:
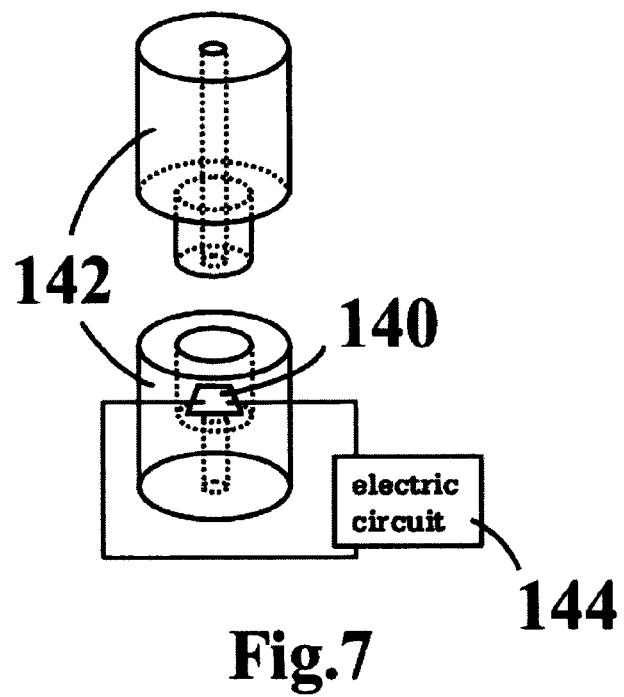
FIG. 7 shows an application of the present invention to column liquid chromatography.

Referring to FIG. 7, in an application of the present invention to column liquid chromatography, the dielectric sensing system comprises a housing 142, a dielectric sensor 140 and an electric circuit 144.

The housing 142 may be made of Teflon or polyetheretherketones, because of their chemical stability against many chemical substances and because they are easily machined. The housing 142 may comprise a hollow block of Teflon or polyetheretherketones, one end of which fits into the bottom of a separation column. Target analytes of interest and other species may flow in solution through the housing 142, where the dielectric sensor 140 is placed.

Figure 8:
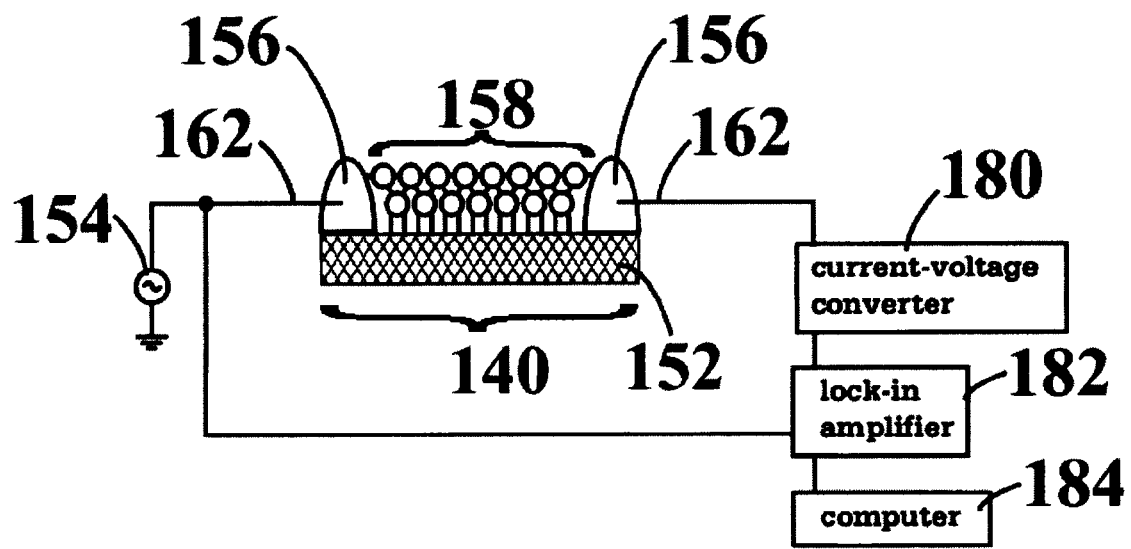
FIG. 8 shows an embodiment of the dielectric sensor in which a glass slide is used as a rigid support.

In one embodiment of the invention, the dielectric sensor 140 for sensing nano-scale target analytes of interest may be prepared by referring to publications by, for example, Musick et al. (1997) and Brust et al. (1998) which are listed among cited references and describe self-assembly of molecularly-linked nanoparticle films in a layer-by-layer fashion. Referring to FIG. 8, a glass slide may be used as a rigid architecture 152. The glass slide is cleaned in a piranha solution (3:1 mixture of sulphuric acid and 30% hydrogen peroxide). Gold pads 156 may then be deposited at the edges of the architecture 152. Then, the architecture 152 is immersed in a solution of insulating molecules such as long chain n-alkanethiols. Next, the architecture 152 is immersed in a solution of bi-functional molecules such as aminosilane. Silane groups attach to a surface of the architecture 152, leaving amino groups available for attaching metallic nanoparticles to the surface of the architecture 152. A film of molecularly-linked nanoparticles 158 may be grown by alternately immersing the architecture 152 in solutions of nanoparticles and dithols. Alkanedithiols and gold nanoparticles may be used for this purpose.

Since the dielectric sensing devices do not require external current flow, long chain molecules may be chosen. In contrast, sensing methods based on conductance or resistance measurements are constrained to use short chain molecules. Also, thicker films are required to enable measurable conductances or resistances. Fewer exposure cycles may be sufficient for said dielectric sensing device, which then contains a plurality of nano-scaled electrodes with nano-scaled inter-electrode separations. Such a device is suitable for detecting nano-scaled target analytes of interest.

The dielectric sensing device may then be inserted in the housing 142 and two wires 162 may be attached to the gold pads 156 on the architecture 152. A sinusoidal voltage 154 of a frequency suitably chosen is applied to a first of the two wires. A second of the two wires is connected to a current-voltage converter 180, the output of which is fed as an input signal into a lock-in amplifier 182. The lock-in amplifier 182 employs phase-lock detection to obtain capacitance of the dielectric sensing device. The detection may be accomplished at the same frequency of the sinusoidal voltage. The frequency may be chosen to maximize signal-to-noise ratio. The phase-lock detection provides information about a phase and magnitude relation between the sinusoidal voltage and the sinusoidal current, thereby providing information about the capacitance of the dielectric sensing device.

Capacitance data from the lock-in amplifier 182 may be recorded using a computer 184. Monitoring of the capacitance data affords real-time information relating to the presence and concentration of target analytes of interest. Electronic circuits components, including a sinusoidal voltage source, a current-voltage converter, and a phase-lock detector may be constructed inexpensively and afford an advantage of excellent portability.

As used herein, the terms "comprises" and "comprising" are to be construed as being inclusive and open rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description related to the invention by way of example only. Many variations on the invention will be obvious to those skilled in the art and such obvious variations are within the scope of the invention as described herein whether or not expressly described.

REFERENCES CITED

U.S. Patent Documents

| U.S. Pat. No. | Issued | Inventor |
| --- | --- | --- |
| 4,814,690 | March 1989 | Melcher et at. |
| 4,822,566 | April 1989 | Newman |
| 4,920,047 | April 1990 | Giaever et al. |
| 5,045,798 | September 1991 | Hendrick |
| 5,187,096 | February 1993 | Giaever et al. |
| 5,194,133 | March 1993 | Clark et al. |
| 5,580,435 | December 1996 | Kovacs |
| 5,846,708 | December 1998 | Hollis et al. |
| 6,242,264 B1 | June 2001 | Natan et al. |
| 6,458,327 B1 | October 2002 | Vossmeyer |
| 6,740,518 B1 | May 2004 | Duong et al. |
| 6,764,583 B2 | July 2004 | Miles |
| 6,773,926 B1 | August 2004 | Freund et al. |
| 6,781,817 | August 2004 | Andelman |
| 6,807,842 B2 | October 2004 | Williams et al. |
| 6,824,974 B2 | November 2004 | Pisharody et al. |
| 6,846,639 B2 | January 2005 | Miles et al. |
| 6,905,586 B2 | June 2005 | Lee et al. |
| U.S. Patent Publication | Published | Inventor |
| 2002/0192653 A1 | December 2002 | Stetter et al. |
| 2004/0124084 A1 | July 2004 | Lee et al. |
| 2005/0227373 A1 | October 2005 | Flandre et al. |
| 2006/0216203 A1 | September 2006 | Fuller et al. |

OTHER PUBLICATIONS

Brust et al. "Self-Assembled Gold Nanoparticle Thin Films with Nonmetallic Optical and Electronic Properties" Langmuir (1998) 14, 5425-5429.

Musick et al. "Electrochemical Properties of Colloidal Au-Based Surfaces: Multilayer Assemblies and Seeded Colloid Films" Langmuir (1999) 15, 844-850.

Musick et al. "Stepwise Construction of Conductive Au Colloid Multilayers from Solution" Chem. Mater. (1997) 9, 1499-1501.

Hu et al. "The integration of gold nanoparticles with semiconductive oligomer layer for development of capacitive immunosensor" Sensors and Actuators B (2005) 106, 641-647.

Esselle et al. "Capacitive Sensors for In-Vivo Measurements of the Dielectric Properties of Biological Materials" IEEE Trans. Instru. Meas. (1988) 37, 101-105.

Benningfield et al. "A Commercially Available Dielectric Constant Detector for Liquid Chromatography and Its Applications" J. Chromatog. Sci. (1981) 19, 115-123.

Poppe et al. "Construction of a Permittivity Detector for Liquid Chromatography" J. Chromatog. Sci. (1972) 10, 16A.

Haderka "Role of mobile phase permittivity in the use of the capacitance detectors in liquid chromatography" J. Chromatog. (1970) 52, 213-220.

Haderka "Use of the resonance principle in the permittivity detectors for liquid chromatography" J. Chromatog. (1970) 54, 357-366.

Haderka "The prospects of selective detection by capacitance detectors in liquid chromatography" J. Chromatg. (1971) 57, 181-191.

Fuller et al. "On-Line Process Liquid Exclusion Chromatography Applied to the Production of Styrene-Butadiene Copolymers" J. Chromatg. Sci. (1979) 17, 661-665.

Stelzle et al. "Sensitive detection of protein adsorption to supported lipid bilayers by frequency-dependent capacitance measurements and microelectrophoresis" Biochimica et Biophysica Acta. (1989) 981, 135-142.

Wohltjen et al. "Colloidal Metal-Insulator-Metal Ensemble Chemiresistor Sensor" Anal. Chem. (1998) 70, 2856-2859.

Fishelson et al. "Studies on Charge Transport in Self-Assembled Gold-Dithiol Films Conductivity, Photoconductivity, and Photoelectrochemical Measurements" Langmuir (2001) 17, 403-412.

Joseph et al. "Self-Assembled Gold Nanoparticle/Alkanedithiol Films: Preparation, Electron Microscopy, XPS-Analysis, Charge Transport, and Vapor-Sensing Properties" J. Phys. Chem. B (2003) 107, 7406-7413.

Joseph et al. "Chemiresistor coating from Pt- and Au-nanoparticle/nonanedithiol films: sensitivity to gases and solvent vapors" Sensors and Actuators B (2004) 98, 188-195.

Su et al. "Miniaturized Chemical Multiplexed Sensor Array" J. Am. Chem. Soc. (2003) 125, 9930-9931.

Leopold et al. "Growth, conductivity, and vapor response properties of metal ion-carboxylate linked nanoparticle films" Faraday Discuss. (2004) 125, 63-76.

Joseph et al. "Gold-nanoparticle/organic linker films: self-assembly, electronic and structural characterisation, composition and vapour sensitivity" Faraday Discuss. (2004) 125, 77-97.

Therefore what is claimed is:

1. A sensing device for sensing an analyte, comprising:
   a) a rigid architecture including
      i) a first electrode layer,
      ii) an insulating region located on said first electrode layer,
      iii) a second electrode layer located on said insulating region and having a plurality of apertures therethrough,
      iv) a plurality of open wells in said insulating region aligned with and extending from said apertures in said second electrode layer, said plurality of open wells being configured to provide analytes therein with access to a time-dependent electric field produced by applying a time-dependent voltage between said first and second electrode layers such that when said time-dependent voltage is applied the time-dependent electric field is produced in said plurality of open wells, each of said plurality of open wells having a depth of at least molecular dimensions;
   b) a means for applying the time-dependent voltage between said first and second electrode layers wherein the time-dependent voltage produces a time-dependent response of said sensing device; and
   c) a detection means for detecting a change in the time-dependent response induced by a presence of the analyte in at least one of said plurality of open wells.

2. The sensing device according to claim 1 including at least one chemical and/or biological discrimination element located in said plurality of open wells.

3. The sensing device according to claim 1, wherein the time-dependent electric field oscillates.

4. The sensing device according to claim 1, wherein said detection means for detecting said change in said time-dependent response of said sensing device includes a phase-lock detector.

5. The sensing device according to claim 4, including at least one chemical and/or biological discrimination element located in said plurality of open wells.

6. The sensing device according to claim 1, wherein:
   said insulating region is an insulating layer;
   said first electrode layer comprises a semiconducting layer on which said insulating layer is located; and
   said detection means detects a change in an effective dielectric constant induced by said analyte located in said open wells.

7. The sensing device according to claim 6, wherein said insulating region comprises inorganic and/or organic materials selected from the group consisting of oxides of said first electrode layer, silicon oxides, silicon nitrides, self-assembled films, and polymers grown or deposited on said semiconducting layer.

8. The sensing device according to claim 6, wherein said insulating layer is coated with a material having a larger dielectric constant than that of said insulating layer, said material being a scaffolding for attaching thereto chemical and/or biological discrimination elements.

9. The sensing device according to claim 1, including at least one of a thin granular film or a self-assembled network of nanoparticles.

10. The sensing device according to claim 1 wherein said sensing device includes means for enabling analytes and other species from a separation apparatus to flow to said sensing device to be sensed.

11. The sensing device according to claim 1 wherein said detection means and said first electrode layer form an electrically integrated system.

12. The sensing device according to claim 2 wherein said chemical and/or biological discrimination element comprises at least one of unfunctionalized molecules, mono-functionalized molecules, bi-functionalized molecules, poly-functionalized molecules, oligomers, polymers, catalysts, cells, bacteria, viruses, enzymes, proteins, heptans, saccharides, lipids, glycogens, enzyme inhibitors, enzyme substrates, neurotransmitters, hormones, antigens, antibodies, DNA, and RNA.

13. A separation apparatus, comprising:
   a material through which an analyte and other species travel at different rates;
   a sensing system located downstream of said material for sensing the analyte comprising:

a) a rigid architecture including
  i) a first electrode layer,
  ii) an insulating region located on said first electrode layer,
  iii) a second electrode layer located on said insulating region and having a plurality of apertures therethrough,
  iv) a plurality of open wells in said insulating region aligned with and extending from said apertures in said second electrode layer, each of said plurality of open wells having a depth of at least molecular dimensions;
b) a time-dependent electric field produced by applying a time-dependent voltage between said first and second electrode layers, wherein the time-dependent voltage produces a time-dependent response of said sensing system, and
wherein said plurality of open wells are configured to provide analytes therein with access to the time-dependent electric field such that when said time-dependent voltage is applied the time-dependent electric field is produced in said plurality of open wells; and
c) a means for detecting a change in the time-dependent response induced by a presence of the analyte in at least one of said plurality of open wells.

14. The separation apparatus according to claim 13 including at least one chemical and/or biological discrimination element located in said plurality of open wells.

15. The separation apparatus according to claims 14, wherein the chemical and/or biological discrimination element comprises at least one of unfunctionalized molecules, mono-functionalized molecules, bi-functionalized molecules, poly-functionalized molecules, oligomers, polymers, catalysts, cells, bacteria, viruses, enzymes, proteins, heptans, saccharides, lipids, glycogens, enzyme inhibitors, enzyme substrates, neurotransmitters, hormones, antigens, antibodies, DNA, and RNA.

16. The separation apparatus according to claim 13, wherein the time dependent electric field oscillates.

17. The separation apparatus according to claim 13, wherein said means for detecting the change in the time-dependent response of said sensing system includes a phase-lock detector.

18. The separation apparatus according to claim 14, wherein
said insulating region is an insulating layer;
said first electrode layer comprises a semiconducting layer on which said insulating layer is located; and
said means for detecting the change in the time-dependent response induced by said analyte located in said open wells detects a change in an effective dielectric constant.

19. The separation apparatus according to claim 14, insulating region comprises inorganic and/or organic materials selected from the group consisting of oxides of said first electrode layer, silicon oxides, silicon nitrides, self-assembled films, and polymers grown or deposited on said semiconducting layer.

20. The separation apparatus according to claim 18, wherein said insulating layer is coated with a material having a larger dielectric constant than that of said insulating layer, said material being a scaffolding for attaching thereto chemical and/or biological discrimination elements.

21. The separation apparatus according to claim 14, including at least one of a thin granular film or a self-assembled network of nanoparticles.

22. A method for sensing an analyte, comprising the steps of;
providing a rigid architecture including
  i) a first electrode layer,
  ii) an insulating region located on said first electrode layer,
  iii) a second electrode layer located on said insulating region and having a plurality of apertures therethrough,
  iv) a plurality of open wells in said insulating region aligned with and extending from said apertures in said second electrode layer, said plurality of open wells being configured to provide analytes therein with access to a time-dependent electric field produced by applying a time-dependent voltage between said first and second electrode layers such that when said time-dependent voltage is applied the time-dependent electric field is produced in said plurality of open wells, each of said plurality of open wells having a depth of at least molecular dimensions;
applying the time-dependent voltage between said first and second electrode layers wherein the time-dependent voltage produces a time-dependent response of said sensing device;
detecting a change in the time-dependent response induced by a presence of the analyte in at least one of said plurality of open wells; and
determining a presence or absence of said analyte based on said change in the time-dependent response.

23. The method according to claim 22 including at least one chemical and/or biological discrimination element located in said plurality of open wells.

24. The method according to claim 23 wherein the chemical and/or biological discrimination element comprises at least one of unfunctionalized molecules, mono-functionalized molecules, bi-functionalized molecules, poly-functionalized molecules, oligomers, polymers, catalysts, cells, bacteria, viruses, enzymes, proteins, heptans, saccharides, lipids, glycogens, enzyme inhibitors, enzyme substrates, neurotransmitters, hormones, antigens, antibodies, DNA, and RNA.

25. The method according to claim 22, wherein:
said insulating region is an insulating layer;
said first electrode layer comprises a semiconducting layer on which said insulating layer is located; and
said detecting step detects change in an effective dielectric constant induced by said analyte located in said open wells.

26. The method according to claim 25, wherein said insulating region comprises inorganic and/or organic materials selected from the group consisting of oxides of said first electrode layer, silicon oxides, silicon nitrides, self-assembled films and polymers grown or deposited on said semiconducting layer.

27. The method according to claim 25, wherein said insulating layer is coated with a material having a larger dielectric constant than that of said insulating layer, said material being a scaffolding for attaching thereto chemical and/or biological discrimination elements.

28. The method in claim 22, wherein the rigid architecture includes at least one of a thin granular film and a self-assembled network of nanoparticles.

29. The method according to claim 28, wherein said nanoparticles are electrically conductive nanoparticles.

30. The method according to claim 22, wherein the time dependent electric field oscillates.

31. The method according to claim 22, wherein said step of detecting said change in said time-dependent response is performed using a phase-lock detector.

32. The sensing device according to claim 9, wherein said nanoparticles are electrically conductive nanoparticles.

33. The separation apparatus according to claim 21, wherein said nanoparticles are electrically conductive nanoparticles.

34. The method according to claim 22 including flowing the analytes and other species from a separation apparatus to flow over said rigid architecture.

\* \* \* \* \*